United States Patent
Fritz et al.

(10) Patent No.: US 10,465,132 B2
(45) Date of Patent: Nov. 5, 2019

(54) METHOD FOR SEPARATING A HYDROCARBON MIXTURE, SEPARATING PLANT AND STEAM CRACKING PLANT

(71) Applicant: Linde Aktiengesellschaft, München (DE)

(72) Inventors: Helmut Fritz, München (DE); Tobias Sinn, München (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 15/036,389

(22) PCT Filed: Oct. 30, 2014

(86) PCT No.: PCT/EP2014/073284
§ 371 (c)(1),
(2) Date: May 12, 2016

(87) PCT Pub. No.: WO2015/071105
PCT Pub. Date: May 21, 2015

(65) Prior Publication Data
US 2016/0319206 A1    Nov. 3, 2016

(30) Foreign Application Priority Data
Nov. 14, 2013    (EP) .................................... 13005355

(51) Int. Cl.
*C10G 70/04*    (2006.01)
*C07C 7/00*    (2006.01)
(Continued)

(52) U.S. Cl.
CPC .............. *C10G 70/04* (2013.01); *B01D 3/14* (2013.01); *B01D 3/324* (2013.01); *C07C 7/005* (2013.01);
(Continued)

(58) Field of Classification Search
CPC .... C10G 70/04; C10G 70/041; C10G 70/043; B01D 3/14; B01D 3/143–148; B01D 3/324
See application file for complete search history.

(56) References Cited

U.S. PATENT DOCUMENTS 3,150,199 A * 9/1964 Greco ........................ C07C 7/04
585/258
4,720,293 A * 1/1988 Rowles ...................... C07C 7/04
62/630
(Continued)

FOREIGN PATENT DOCUMENTS

CN    1112911 A    12/1995
CN    1175997 A    3/1998
(Continued)

OTHER PUBLICATIONS

PCT/EP2014/073284 English Translation of the International Preliminary Report on Patentability, dated Mar. 16, 2016, 17 pages.
(Continued)

*Primary Examiner* — Philip Y Louie
*Assistant Examiner* — Alyssa L Cepluch
(74) *Attorney, Agent, or Firm* — Lathrop Gage LLP

(57) ABSTRACT

A method for separating a hydrocarbon mixture, which is obtained at least in part by steam cracking and which contains at least hydrocarbons having one, two and three carbon atoms, including ethane and ethylene, a first fraction initially being obtained from the hydrocarbon mixture by separating off other components at least in part, said fraction containing the predominant part of the hydrocarbons having two or more carbon atoms previously contained in the hydrocarbon mixture or the predominant part of the hydrocarbons having two or fewer carbon atoms previously contained in the hydrocarbon mixture, further fractions subsequently being obtained from the first fraction. A fraction
(Continued)

containing ethane is separated off in an amount which reduces the ethane content in the first fraction to less than 25%, the fraction containing ethane being low in or free from other hydrocarbons having two carbon atoms.

12 Claims, 3 Drawing Sheets

(51) Int. Cl.
*B01D 3/14* (2006.01)
*B01D 3/32* (2006.01)
*C10G 9/00* (2006.01)
*C10G 70/02* (2006.01)
*F25J 3/02* (2006.01)

(52) U.S. Cl.
CPC ............... *C10G 9/00* (2013.01); *C10G 70/02* (2013.01); *F25J 3/0219* (2013.01); *F25J 3/0233* (2013.01); *F25J 3/0238* (2013.01); *F25J 3/0242* (2013.01); *F25J 2210/12* (2013.01); *F25J 2215/62* (2013.01)

(56) References Cited

U.S. PATENT DOCUMENTS

| | | | |
|---|---|---|---|
| 5,361,589 A | 11/1994 | Howard et al. | |
| 5,372,009 A * | 12/1994 | Kaufman | C10G 70/04 62/630 |
| 5,960,643 A * | 10/1999 | Kuechler | C07C 7/005 62/620 |
| 7,437,891 B2 * | 10/2008 | Reyneke | C07C 7/005 208/350 |
| 2011/0137095 A1 * | 6/2011 | Chewter | C01B 3/24 585/323 |
| 2013/0225884 A1 * | 8/2013 | Weinberger | F25J 3/0219 585/16 |

FOREIGN PATENT DOCUMENTS

| | | |
|---|---|---|
| CN | 1241991 A | 1/2000 |
| CN | 101263215 A | 9/2008 |
| CN | 102753656 A | 10/2012 |
| EP | 2336272 A1 | 6/2011 |
| JP | H07258119 A | 10/1995 |
| JP | 2006188510 A | 7/2006 |
| TW | 200628445 A | 8/2016 |
| WO | 1997/015795 A1 | 5/1997 |
| WO | 2007/018517 A1 | 2/2007 |

OTHER PUBLICATIONS

PCT/EP2014/073284 English Translation of the International Search Report dated Apr. 15, 2015, 2 pages.
Office Action corresponding to Chinese Patent Application No. 201480062241.7, dated Mar. 27, 2017—English ranslation provided only, 15 pages.
Taiwan Patent Application No. 103139235 Office Action dated Feb. 23, 2018, 12 pages.
Chinese Patent Application No. 201480062241.7 Office Action dated May 18, 2018, 9 pages.
Chinese Patent Application No. 201480062241.7 English translation of Office Action dated May 18, 2018, 14 pages.
Japanese Patent Application No. 2016-530929 Office Action dated Sep. 18, 2018 with English translation, 8 pages.
Chinese Patent Application No. 201480062241.7 Office Action dated Jul. 23, 2019 with English translation, 25 pages.

* cited by examiner

METHOD FOR SEPARATING A HYDROCARBON MIXTURE, SEPARATING PLANT AND STEAM CRACKING PLANT

The invention relates to a method for separating a hydrocarbon mixture, to a corresponding separation system, to a steam cracking system comprising a separation system of this type, and to a method for retrofitting a steam cracking system, in accordance with the preambles of the independent claims.

PRIOR ART

Methods and devices for steam cracking hydrocarbons are known, and are described for example in the article "Ethylene" in Ullmann's Encyclopedia of Industrial Chemistry, online as of 15 Apr. 2007, DOI 10.1002/14356007.a10_045.pub2.

Steam cracking methods are carried out on a commercial scale in tubular reactors, which can in principle be loaded with a plurality of hydrocarbons and hydrocarbon mixtures, from ethane to gas oil, up to a boiling point of typically 600° C. (known as a furnace charge). Reaction tubes or groups of reaction tubes operated under identical or comparable cracking conditions (see below), or optionally even tube reactors operated in uniform cracking conditions as a whole, are denoted as "cracking furnaces" in the following. Thus, in the usage found herein, a cracking furnace is a constructional unit used for steam cracking which exposes a furnace charge to identical or comparable cracking conditions. A system for steam cracking may comprise one or more cracking furnaces of this type.

The respective furnace charge is reacted at least in part during steam cracking in the cracking furnace or furnaces, leading to crude gas being obtained. The crude gas of a plurality of cracking furnaces can be combined and, as is described in greater detail in reference to FIGS. 1A and 1B, subjected to a series of post-treatment steps. Post-treatment steps of this type initially include processing the crude gas, for example by quenching, cooling and drying, leading to cracked gas being obtained. Occasionally crude gas is also referred to as cracked gas and vice versa.

The cracked gas is a hydrocarbon mixture comprising hydrocarbons of various chain lengths and structures. So as to obtain the desired products from the cracked gas, it therefore has to be separated. Various methods are known in the art for this purpose and are described in detail for example in the aforementioned article "Ethylene" in Ullmann's Encyclopedia of Industrial Chemistry. Methods for processing a cracked gas are also disclosed for example in U.S. Pat. Nos. 5,372,009 A and 5,361,589 A.

As is also described below, in a steam cracking system the furnace charge of one or more cracking furnaces is generally composed of one or more fresh charges supplied from the outside and of one or more recycled streams or recycled fractions separated off from the cracked gas.

The composition of the cracked gas depends inter alia on the composition of the respectively used furnace charge. The more ethane-rich the fresh charge or charges used in the furnace charge, the more ethane the cracked gas will also contain. Thus, much higher proportions of ethane are found in the cracked gas again if ethane-rich hydrocarbon mixtures are used than if low-ethane hydrocarbon mixtures such as naphtha are used.

However, it may be desirable for economic reasons to use ethane-rich hydrocarbon mixtures. These accumulate in large amounts during natural gas production, inter alia in the form of natural gas liquids (NGLs), and can be converted to useful products by steam cracking. The same applies to the comparatively ethane-rich shale gas provided by fracking methods.

A steam cracking system set up exclusively for processing ethane-free fresh charges such as naphtha cannot readily be converted for one or more fresh charges which contain non-negligible amounts of ethane, since the comparatively high ethane content in the cracked gas can only be dealt with during the subsequent separation with considerable additional constructional outlay.

For example, in this context multiple series of separation units have to be provided, or the capacity of the series of separation units has to be increased with considerable effort.

Of course, problems of this type do not only occur if conventional fresh charges such as naphtha are completely replaced with more ethane-rich fresh charges, but also if more ethane-rich fresh charges are only used in part. This negates any economic advantages that might be achieved. The invention aims to remedy this situation.

DISCLOSURE OF THE INVENTION

In the context of the present invention, the stated object is achieved by a method for separating a hydrocarbon mixture, a corresponding separation system, a steam cracking system comprising a separation system of this type, and a method for retrofitting a steam cracking system having the features of the independent claims. Preferred configurations form the subject matter of the dependent claims and of the following description.

Before the features and advantages of the present invention are described, the underlying principles and the terminology used will be explained.

Herein, the term "furnace charge", already used in the above, denotes one or more liquid and/or gaseous streams which are supplied to one or more cracking furnaces. Streams obtained by a steam cracking method of this type may also, as described in the following, be fed back into one or more cracking furnaces and used as a furnace charge again. As described, a plurality of hydrocarbons and hydrocarbon mixtures from ethane to gas oil, up to a boiling point of typically 600° C., are suitable as a furnace charge. As stated, the present invention relates predominantly to the use of furnace charges which include fresh charges having a comparatively high ethane content.

As stated, a "fresh charge" of this type is supplied from outside the system and is obtained for example from one or more petroleum fractions, natural gas components having two to four carbon atoms, including ethane, and/or natural gas liquids. A furnace charge may also consist of one or more "recycled streams", in other words streams which are generated in the system itself and fed back into a corresponding cracking furnace. A furnace charge may also consist of a mixture of one or more fresh charges with one or more recycled streams.

In the usage found herein, a "steam cracking system" comprises one or more cracking furnaces which are operated in identical or different cracking conditions and can be loaded with identical or different furnace charges, and a "separation system", which is set up to separate an obtained cracked gas, typically comprises a series of distillation columns, and is set up to separate the cracked gas into a plurality of fractions on the basis of the boiling points of the obtained hydrocarbons.

In the art, abbreviations are used for fractions of this type, specifying the carbon number of the hydrocarbons which are predominantly or exclusively contained in each case. Thus, a "C1 fraction" is a fraction which predominantly or exclusively contains methane (but by convention sometimes also hydrogen, in which case it may also be referred to as a "C1minus fraction"). By contrast, a "C2 fraction" predominantly or exclusively contains ethane, ethylene and/or acetylene. A "C3 fraction" predominantly contains propane, propylene, methylacetylene and/or propadiene. A "C4 fraction" predominantly or exclusively contains butane, butene, butadiene and/or butyne, the respective isomers potentially being contained in different proportions depending on the source of the C4 fraction. The same applies to a "C5 fraction" and higher fractions. A plurality of fractions of this type may also be combined as regards the method and/or as regards the terminology. For example, a "C2plus fraction" predominantly or exclusively contains hydrocarbons having two or more carbon atoms, and a "C2minus fraction" predominantly or exclusively contains hydrocarbons having one or two carbon atoms.

In the usage found herein, liquid and gaseous streams may be rich or low in one or more components, where "rich" may mean a content of at least 90%, 95%, 99%, 99.5%, 99.9%, 99.99% or 99.999% and "low" may mean a content of at most 10%, 5%, 1%, 0.1%, 0.01% or 0.001% by molarity, by weight or by volume. The term "predominantly" means a content of at least 50%, 60%, 70%, 80% or 90% or corresponds to the term "rich". In the usage found herein, liquid and gaseous streams may further be enriched in or depleted of one or more components, these terms relating to a corresponding content in a starting mixture from which the liquid or gaseous stream was obtained. The liquid or gaseous stream is "enriched" if it contains at least 1.1 times, 1.5 times, 2 times, 5 times, 10 times, 100 times or 1000 times the content, and "depleted" if it contains at most 0.9 times, 0.5 times, 0.1 times, 0.01 times or 0.001 times the content of a corresponding component by comparison with the starting mixture.

In the usage found herein, if a fresh charge contains a "non-negligible amount" of ethane, it has an ethane content which is more than for example 5%, 10%, 20%, 30% or 40%. In principle, pure ethane could even be used as the fresh charge, for example together with other heavier fresh charges such as naphtha. Typically, however, the upper limit on the ethane content of fresh charges of this type is 90%, 80%, 70%, 60% or 50%. For example, shale gas and natural gas liquids are fresh charges which contain a non-negligible amount of ethane.

In this application, percentages may be by volume, molarity or mass. Pressures are given as absolute pressures.

A stream may be "derived" from another stream, for example by dilution, concentration, enrichment, depletion, separation or reaction of any desired components, by separation steps, or else by combination with at least one further stream. A derived stream may also be formed by dividing a starting stream into at least two substreams, in which case each substream, or even a remaining stream after another stream is separated off, is a derived stream of this type.

Advantages of the Invention

The present invention starts from a known method for separating a hydrocarbon mixture obtained at least in part by steam cracking. As stated above, a hydrocarbon mixture of this type is denoted as a cracked gas or crude gas and is subjected to one or more processing steps. The hydrocarbon mixture comprises at least hydrocarbons having one, two and three carbon atoms, including ethane and ethylene. As stated, the amounts of ethane in a cracked gas of this type are increased during steam cracking if fresh charges are used which contain a non-negligible amount of ethane.

Even if hydrocarbon mixtures predominantly containing ethane are used as furnace charges for the steam cracking, the cracked gas will contain hydrocarbons having more than three carbon atoms. As stated, conventional fresh charges such as naphtha are also not necessarily completely replaced with ethane-rich fresh charges, and so for this reason too significant amounts of hydrocarbons having more than three carbon atoms are typically contained in the cracked gas.

Thus, the separation to be undertaken does not necessarily differ qualitatively, but rather may differ quantitatively (in other words as regards the respective proportions of the fractions to be separated), when fresh charges which contain non-negligible amounts of ethane are used in the steam cracking.

Initially, a fraction denoted herein as the "first fraction" is obtained from the hydrocarbon mixture by separating off other components at least in part. As is described in greater detail in the following, the prior art distinguishes between "demethaniser-first" and "deethaniser-first" methods. Generally speaking, these comprise initially obtaining a "first" fraction, which contains either the predominant part of the hydrocarbons having two or more carbon atoms previously contained in the hydrocarbon mixture or else the predominant part of the hydrocarbons having two or fewer carbon atoms previously contained in the hydrocarbon mixture, from the hydrocarbon mixture by separating off other components at least in part.

This first fraction contains the predominant proportion of the hydrocarbons having two or more carbon atoms contained in the hydrocarbon mixture if it has previously passed through a demethaniser, in other words lighter components (methane and if applicable hydrogen) have been separated off. By contrast, if hydrocarbons having three or more carbon atoms are initially separated off from a hydrocarbon mixture of this type in a deethaniser, a first fraction is left which contains the predominant part of the hydrocarbons having two or fewer carbon atoms previously contained in the hydrocarbon mixture.

The method according to the invention is thus suitable both for demethaniser-first and for deethaniser-first methods and for corresponding variants of these methods, such as are generally known, since the fraction denoted herein as the "first fraction", which in this context is present downstream from the separation process (demethaniser or deethaniser), in each case contains the entirety or the predominant proportion of the amount of ethane contained in the original hydrocarbon mixture (cracked gas or crude gas). As has been stated repeatedly, this amount of ethane is greatly increased if fresh charges which contain a non-negligible amount of ethane are used.

In both demethaniser-first and deethaniser-first methods, further fractions are subsequently obtained from the described first fraction. These further fractions may be fractions comprising hydrocarbons of a varying and/or uniform chain length and/or identical empirical formula and/or structural formula. For instance, a typical example of further fractions of this type would be ethylene and/or butadiene and/or fractions of a plurality of hydrocarbons of varying and/or uniform chain length which are drawn out of a system of this type and/or fed back into a steam cracking process (recycled fractions). A recycled fraction of this type is typically ethane separated off from the cracked gas.

As has also been stated repeatedly, separation systems which are formed as part of steam cracking systems for processing low-ethane fresh charges may often not be set up to deal with relatively high amounts of ethane in the hydrocarbon mixture obtained (cracked or crude gas), in terms of capacity or the separation process, when processing more ethane-rich fresh charges.

The invention provides that a fraction containing ethane is also separated off during or after the separation of the other components at least in part from the original hydrocarbon mixture, in other words during or after the formation of the first fraction, in particular downstream from a demethaniser or in parallel with or downstream from a deethaniser, in such a way that the ethane content in the first fraction is reduced to less than 25%. The separation may for example take place before the further fractions are subsequently obtained. If the separation takes place during the separation of the other components at least in part from the original hydrocarbon mixture, for example in parallel with a separation step of this type, the first fraction is already formed with a correspondingly reduced ethane content; if the separation takes place downstream therefrom, the ethane content of the first fraction is reduced. In this way, the ethane content of the first fraction can for example be adapted to the ethane contents obtained when using low-ethane fresh charges. When the fresh charge or charges are changed, this makes it possible to carry on operating the separation system in a largely unchanged manner apart from the measures provided by the invention.

In other words, by means of the separation according to the invention of the fraction containing ethane, the ethane content of the first fraction is lowered to such an extent that even existing separation systems are able to process said fraction. Instead of the increase in capacity of the downstream separation units for obtaining the further fractions, which would otherwise be necessary for dealing with the increased amount of ethane, the method according to the invention makes comparatively simple and cost-effective reduction of increased ethane contents possible.

As well as ethane, the fraction containing ethane may contain further components which depend on the method used for obtaining the first fraction. In this way, a fraction of this type containing ethane may for example contain hydrocarbons having three or more carbon atoms if a demethaniser-first method is used. The fraction containing ethane may also consist predominantly (within the meaning defined above) of ethane.

In any event, the fraction predominantly containing ethane is low, within the meaning above, in other hydrocarbons having two carbon atoms, preferably free thereof. Other hydrocarbon atoms of this type having two carbon atoms are obtained from the first fraction in downstream separation steps. For example, ethylene is contained at at most 1.5%, 1.0%, 5000 ppm, 4000 ppm or 3000 ppm.

A method according to the invention comprises in particular specifying an ethane content which is acceptable in a separation system used for carrying out the method. The values which typically occur when low-ethane fresh charges are processed may also be used for a specification of this type. The amount of the fraction containing ethane is adapted in accordance therewith. Thus, as described, the amount of the ethane in the first fraction is reduced to such an extent that the tolerable ethane content in the downstream devices or separation units can be adhered to. This is for example also an ethane content of less than 20%, 17%, 15%, 13% or 10%.

The ethane content in the first fraction after the fraction predominantly containing ethane has been separated off also defines the total amount or volume stream thereof, in such a way that an amount of ethane which is "acceptable" here is also dependent for example on the corresponding hydraulic limitations of existing components. Hydrogenation devices, such as are shown in the accompanying drawings, also have a limited maximum throughput, and so a maximum acceptable amount of ethane (which defines the amount or volume stream of the respective stream) must not be exceeded here either.

As described, the fraction containing ethane may in particular also contain further hydrocarbons, in particular traces of ethylene and acetylene and potentially other hydrocarbons having three or more carbon atoms. These can be separated off from the fraction containing ethane, in such a way that a pure ethane fraction or an ethane-rich fraction is subsequently present.

It is advantageous to process the fraction containing ethane by steam cracking, at least in part, meaning that corresponding ethane is passed through the used steam cracking system as a recycled stream.

As explained above, the method according to the invention is suitable both for demethaniser-first and for deethaniser-first methods. In a demethaniser-first method, as explained previously, to obtain the first fraction from the hydrocarbon mixture a fraction is separated off which contains the predominant proportion of the methane and hydrogen contained in said mixture (in other words a C1minus fraction is separated off). The first fraction therefore contains the predominant proportion of the hydrocarbons having two or more carbon atoms contained in the hydrocarbon mixture.

The method according to the invention is also suitable for the described deethaniser-first method. In methods of this type, after an upstream crude gas compression, the hydrocarbon mixture is for example cooled to a temperature of −15 to −30° C. Non-condensable components and the accumulating condensates are passed to a deethaniser in which a C2minus fraction is separated off from the remaining C3plus fraction. In this case, the C2minus fraction is denoted as the first fraction. As described, according to the invention the fraction containing ethane is separated out from this. However, it may also be separated out in parallel with the deethaniser. The C2minus stream obtained is typically subjected to C2 hydrogenation, in which acetylenes react with the excess hydrogen. Since according to the invention some of the ethane has already been separated off at this point, it does not interfere in particular with this hydrogenation process because of the sheer amount thereof.

The C2minus stream, which is acetylene-free as a result of the hydrogenation, is subsequently cooled and condensed in part, until hydrogen on the one hand and the remaining hydrocarbons (methane, ethane and ethylene) on the other hand are substantially separated from one another. The condensates obtained, which predominantly contain methane, ethane and ethylene, are subsequently fed into a methane column, in which C2 hydrocarbons are separated from methane. As a result of the partial previous separation of ethane according to the invention, upstream from a methane column of this type, there are smaller volumes to be dealt with here too.

In the described methane column, a liquid ethane/ethylene mixture is obtained which is fed into a C2 splitter, in which ethane is substantially separated from ethylene. Because of the partial removal of ethane according to the invention, there are smaller volumes to be dealt with here too.

A separation system of this type comprises a first separation unit, which is set up so as initially to obtain a first fraction from the hydrocarbon mixture, by separating off other components at least in part, said fraction containing either the predominant part of the hydrocarbons having two or more carbon atoms previously contained in the hydrocarbon mixture or the predominant part of the hydrocarbons having two or fewer carbon atoms previously contained in the hydrocarbon mixture. Further separation units are provided, which are set up so as subsequently to obtain further fractions from the first fraction. According to the invention, the separation system comprises an additional separation unit which is set up to separate off a fraction containing ethane during or after the at least partial separation of the other components from the hydrocarbon mixture in an amount which reduces the ethane content in the first fraction to less than 25%. The properties of this fraction which predominantly contains ethane were described in detail above.

The additional separation unit may be in the form of a distillation column, which preferably comprises 60 to 120, for example 70 to 100, in particular 80 to 90 trays. This dimensioning is suitable in particular for a demethaniser-first method. The operating pressures and operating temperatures which are advantageously used are based on the process environment and the entry point to the respective fractionation sequence.

Advantageously, a separation system of this type is set up for carrying out a method as described above.

The invention also relates to a steam cracking system comprising at least one cracking furnace, which is set up for preparing a hydrocarbon mixture which contains at least hydrocarbons having one, two and three carbon atoms, including ethane and ethylene. This comprises at least one separation system as described above and benefits from the advantages thereof in the same way.

In particular, the present invention comprises a method for retrofitting a steam cracking system, which is set up to process one or more exclusively low-ethane fresh charges, to process one or more fresh charges which contain a non-negligible amount of ethane. The steam cracking system is equipped with a separation unit which is set up to obtain, by steam cracking a furnace charge formed using the fresh charge or charges, a hydrocarbon mixture which contains at least hydrocarbons having one, two and three carbon atoms, including ethane and ethylene. It is further set up so as initially to obtain a first fraction from this hydrocarbon mixture, by separating out other components at least in part, said fraction containing either the predominant part of the hydrocarbons having two or more carbon atoms previously contained in the hydrocarbon mixture or the predominant part of the hydrocarbons having two or fewer carbon atoms contained in the hydrocarbon mixture (in other words for a demethaniser-first or a deethaniser-first method). The steam cracking system further comprises further separation units, which are set up so as subsequently to obtain further fractions from the first fraction. The retrofitting according to the invention comprises providing an additional separation unit, upstream from the further separation units, which is set up to separate off a fraction predominantly containing ethane during or after the at least partial separation of the other components from the hydrocarbon mixture in an amount which reduces the ethane content in the first fraction to less than 25%. Features of an additional separation unit of this type were specified previously.

In the following, the invention is described in relation to the prior art with reference to the accompanying drawings.

BRIEF DESCRIPTION OF THE DRAWINGS

Corresponding elements are provided with identical reference signs in the drawings, and for brevity are not described more than once.

DETAILED DESCRIPTION OF THE DRAWINGS

Figure 1A:
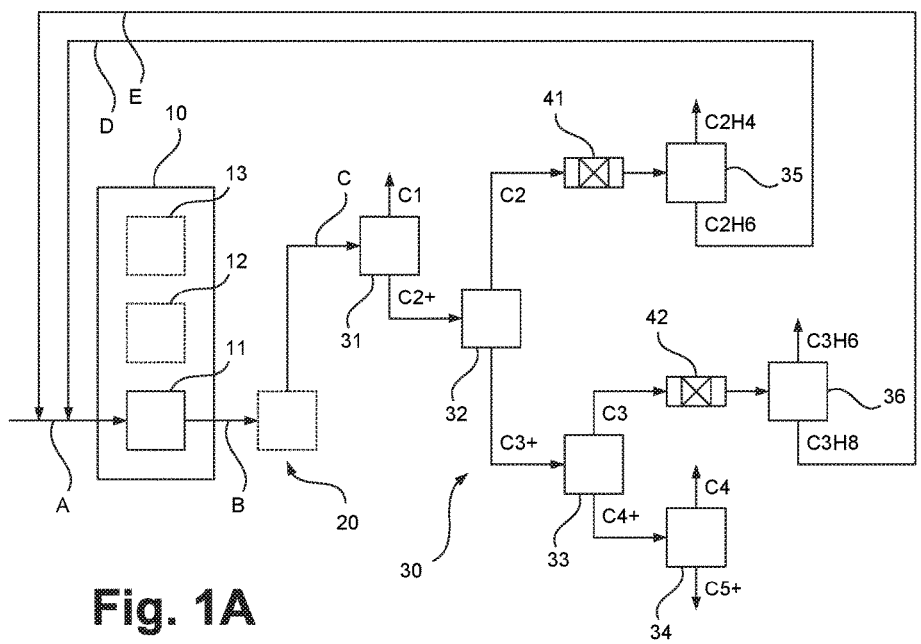
FIG. 1A schematically shows the sequence of a method for producing hydrocarbon products in accordance with the prior art.

FIG. 1A shows in the form of a schematic stream chart the sequence of a method for producing hydrocarbon products by steam cracking and subsequent separation of an obtained cracked gas into fractions in accordance with the prior art.

The central part of the method is a steam cracking process 10, which can be carried out using one or more cracking furnaces 11 to 13. Only the operation of the cracking furnace 11 is described in the following; the further cracking furnaces 12 and 13 may operate in a corresponding manner.

The cracking furnace 11 is loaded with a stream A as a furnace charge, which may in part be a fresh charge provided from sources outside the system, and in part be a recycled stream obtained within the method itself. The other cracking furnaces 12 and 13 may also be charged with corresponding streams. Different streams may also be fed into different furnaces 11 to 13, one stream may be divided between a plurality of cracking furnaces, or a plurality of substreams may be combined into a combined stream which is for example supplied to one of the cracking furnaces 11 to 13 as a stream A.

As a result of the steam cracking in the steam cracking process 10, a crude gas stream B is obtained, sometimes already referred to at this stage as a cracked gas stream. The crude gas stream B is processed in a series of processing steps (not shown) of a processing process 20, for example subjected to oil quenching, prefractionated, compressed, cooled further and dried.

Figure 1B:
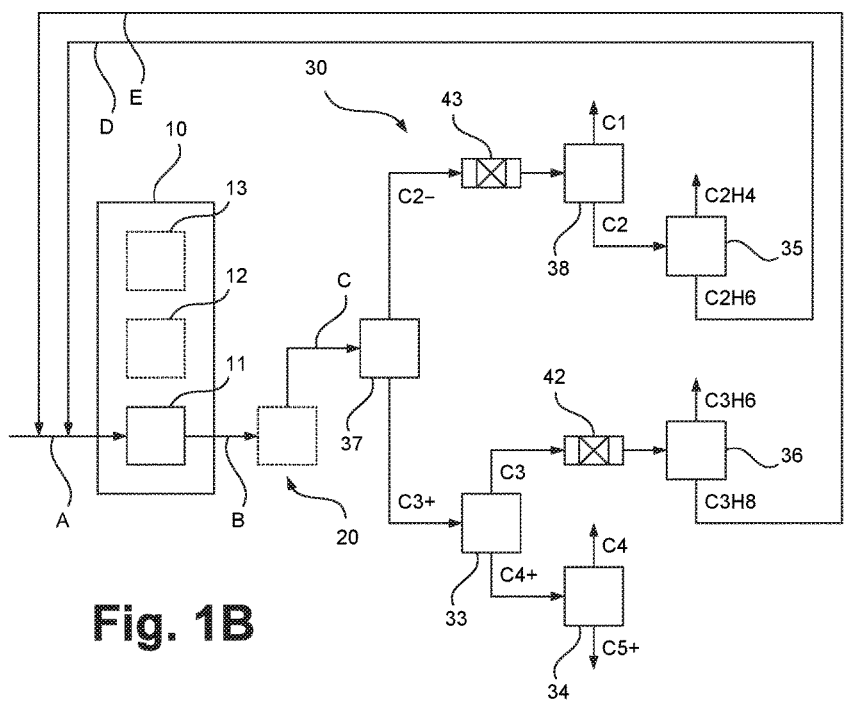
FIG. 1B schematically shows the sequence of a method for producing hydrocarbon products in accordance with the prior art.

The correspondingly treated stream B, the actual cracked gas C, and thus the hydrocarbon mixture separated in the context of the present invention, are subsequently subjected to a separation process 30. The separation process 30 is implemented in a corresponding separation system. A number of fractions are obtained, and are denoted in accordance with the carbon number or the predominantly contained hydrocarbons, as described above. The separation process 30 shown in FIG. 1A operates by the "demethaniser-first" principle; a further separation process by the "deethaniser-first" principle is shown in FIG. 1B.

In the separation process 30, a C1 or C1minus fraction (denoted by reference sign C1) is initially separated off in gaseous form from the cracked gas C, in a first separation unit 31 (the demethaniser), and may also further contain hydrogen if not already removed previously. This fraction is typically used as a fuel gas. This leaves a liquid C2plus fraction (reference sign C2+), which is transferred into a second separation unit 32 (the deethaniser). In the present application, the C2plus fraction is denoted as the "first" fraction if a demethaniser-first method is used.

In this second separation unit 32, a C2 fraction (reference sign C2) is separated off, in gaseous form, from the C2plus fraction. The C2plus fraction may for example be subjected to a hydrotreatment process 41 to convert acetylene contained therein to ethylene. Subsequently, the C2 fraction is separated out into ethylene (reference sign C2H4) and ethane (reference sign C2H6) in a C2 separation unit 35 (also referred to as a C2 splitter). This ethane can be subjected to the steam cracking process 10 again in one or more cracking furnaces 11 to 13 as a recycled stream D. In the example shown, the recycled streams D and E are added to the stream A. The recycled streams D and E and the stream A may also be passed into different cracking furnaces 11 to 13.

As described, if fresh charges which contain a non-negligible amount of ethane are used, the proportion of ethane in the cracked gas C increases in particular. In existing systems, which are set up for use of exclusively low-ethane fresh charges, the described separation units are not configured for such large amounts of ethane.

A liquid C3plus fraction (reference sign C3+) is left behind in the second separation unit 32, and is passed into a third separation unit 33 (the depropaniser), in which a C3 fraction (reference sign C3) is separated off from the C3plus fraction and for example subjected to a further hydrotreatment process 42, so as to convert methylacetylene in the C3 fraction into propylene. Subsequently, the C3 fraction is separated out into propene (reference sign C3H6) and propane (reference sign C3H8) in a C3 separation unit 36. This propane can be subjected to the steam cracking process 10 again in one or more cracking furnaces 11 to 13 as a recycled stream E, separately or together with other streams. A liquid C4plus fraction (reference sign C4+) is left behind in the third separation unit 33, and is passed into a fourth separation unit 34 (the debutaniser), in which a C4 fraction (reference sign C4) is separated off from the C4plus fraction. A liquid C5plus fraction (reference sign C5+) is left behind.

If exclusively gaseous furnace charges are used, it is possible that no C3plus, C4plus or C5 plus hydrocarbons or much smaller amounts thereof will occur, making it possible to dispense with the last separation units.

Needless to say, all of the fractions shown may also be subjected to suitable post-treatment steps. For example, 1,3-butadiene may be separated out from the C4 hydrocarbon stream, if obtained. Further, additional recycled streams may be used, which may be subjected to the steam cracking process 10 analogously to the recycled streams D and E.

FIG. 1B shows in the form of a schematic flow chart the sequence of an alternative method for producing hydrocarbons by steam cracking in accordance with the prior art. In this case too, the central part of the method is a steam cracking process 10, which can be carried out using one or more cracking furnaces 11 to 13. By contrast with the method of FIG. 1A, in this case the cracked gas C is subjected to a separation process 30 by the "deethaniser-first" principle.

In this case, in the separation process 30, a C2minus fraction (reference sign C2−) is initially separated off, in gaseous form, from the cracked gas C, in a first separation unit 37, and predominantly contains methane, ethane, ethylene and acetylene, and may also further contain hydrogen if not already removed previously. In the present application, the C2minus fraction is denoted as the "first" fraction if a deethaniser-first method is used.

The C2minus fraction may be subjected as a whole to a hydrotreatment process 43 so as to convert acetylene contained therein into ethylene. Subsequently, a C1 fraction is separated off from the C2minus fraction in a C2minus separation unit 38, and used further as above. This leaves a C2 fraction, which is separated out into ethylene and ethane in a C2 separation unit 35 as above. In this case too, this ethane can be subjected to the steam cracking process 10 again in one or more cracking furnaces 11 to 13 as a recycled stream D. In this case too, a liquid C3plus fraction may be left behind in the first separation unit 37, and is treated in the separation units 33 to 36 and optionally the hydrotreatment unit 42, as described previously for FIG. 1.

In this case too, an increased proportion of ethane in the cracked gas is problematic, since the described separation units in systems for exclusively low-ethane fresh charges are not configured for such large amounts of ethane.

A plurality of further method alternatives, which differ in particular in the preparation of the cracked gas C and/or the separation process used, are known to the person skilled in the art, for example from the aforementioned article "Ethylene" in Ullmann's Encyclopedia of Industrial Chemistry.

Figure 2:
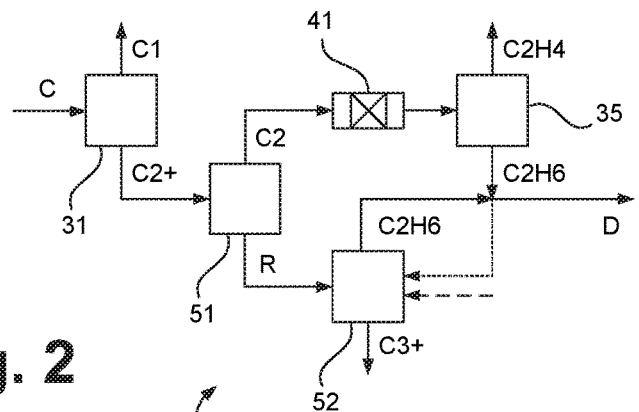
FIG. 2 schematically shows the sequence of a method for separating a hydrocarbon mixture in accordance with an embodiment of the invention.

FIG. 2 shows an approach for solving the problem of the increased proportion of ethane in the cracked gas when fresh charges which contain a non-negligible amount of ethane are used, in accordance with an embodiment of the invention.

The method shown in FIG. 2 is illustrated in the form of a schematic flow chart, and is based on the method shown in FIG. 1A by the demethaniser-first principle. To illustrate the universal applicability of the method according to the embodiment shown, the processes and devices used to produce the cracked gas C have been dispensed with.

A corresponding cracked gas C can, however, be obtained analogously to the method shown by way of example in FIG. 1A. In particular, a cracked gas C of this type comes from one or more cracking furnaces 11 to 13 which are loaded at least in part with a fresh charge as a furnace charge, which comprises a non-negligible amount of ethane.

As described, if exclusively gaseous furnace charges are used, it is possible that no C3plus, C4plus or C5plus hydrocarbons or much smaller amounts thereof will form, and so the processes and devices used for separating corresponding fractions have not been shown. If corresponding hydrocarbons do occur, processes and devices of this type may also be provided in the method shown in FIG. 2.

Instead of a cracked gas C, a fraction of a corresponding cracked gas may be used which results from separation into hydrocarbons having four or more carbon atoms on the one hand and hydrocarbons having three or fewer carbon atoms on the other hand.

The method shown in FIG. 2 in accordance with an embodiment of the invention differs from the method shown in FIG. 1A in particular in the use of an additional separation unit 51 in the separation process 30.

In the additional separation unit 51, for example a distillation column, which has the features specified above, a liquid fraction containing ethane is separated off, but in a demethaniser-first method of the type shown here still contains higher-boiling components, in particular C3plus and higher hydrocarbons. The content is dependent on the furnace charge, as stated, and is relatively low for exclusively gaseous furnace charges. This fraction predominantly containing ethane is denoted by reference sign R in FIG. 2.

This fraction R, which predominantly contains ethane and the higher-boiling components, is also low in other hydrocarbons having two carbon atoms. It is subsequently transferred into a further separation unit 52, in which the higher-boiling C3plus components and the ethane are separated from one another. Part of the ethane or part of a corresponding ethane-rich fraction may also be fed into the separation unit 52 from the previously described separation unit 35 (shown in dotted lines). As a result, energy can be saved and the separation capacity of the separation unit 52, which would be available in any case, can be made use of. In the separation unit 52, which is typically in the form of a distillation column, this ethane fraction can be released from the separation unit 35, in particular at the head. Further, as is illustrated by a dashed arrow, further ethane can be fed into it.

An ethane fraction obtained in the separation unit 52, for example a head product of a corresponding distillation column, can be drawn off, united with further streams, and fed back into a cracking process, as illustrated previously using the stream D.

The further stream obtained in the separation unit 51, here denoted as C2, is the proportion of the C2plus fraction left behind after the fraction R predominantly containing ethane (and comprising the C3plus hydrocarbons) is separated off, and can be adjusted to any desired ethane content by way of the separation. Thus, the separation units arranged downstream from the separation unit 51 (as shown in FIG. 1A) do not need to be changed when a corresponding cracking system is converted from low-ethane to (more) ethane-rich fresh charges.

The function of the additional separating unit 51 thus corresponds in part to the function of the separation unit 32 of a conventional method (cf. FIG. 1A), but in the separation unit 51, instead of a "pure" C3plus fraction, a C3plus fraction comprising a non-negligible proportion of ethane (specifically the repeatedly mentioned fraction containing ethane) is separated off. The function of the separation unit 52 also corresponds in part to the function of the separation unit 32 of the conventional method, but with the difference that in the separation unit 52 comparatively pure ethane is separated from the C3plus hydrocarbons. In functional terms, this is a deethaniser, which would be present in any case.

Figure 3:
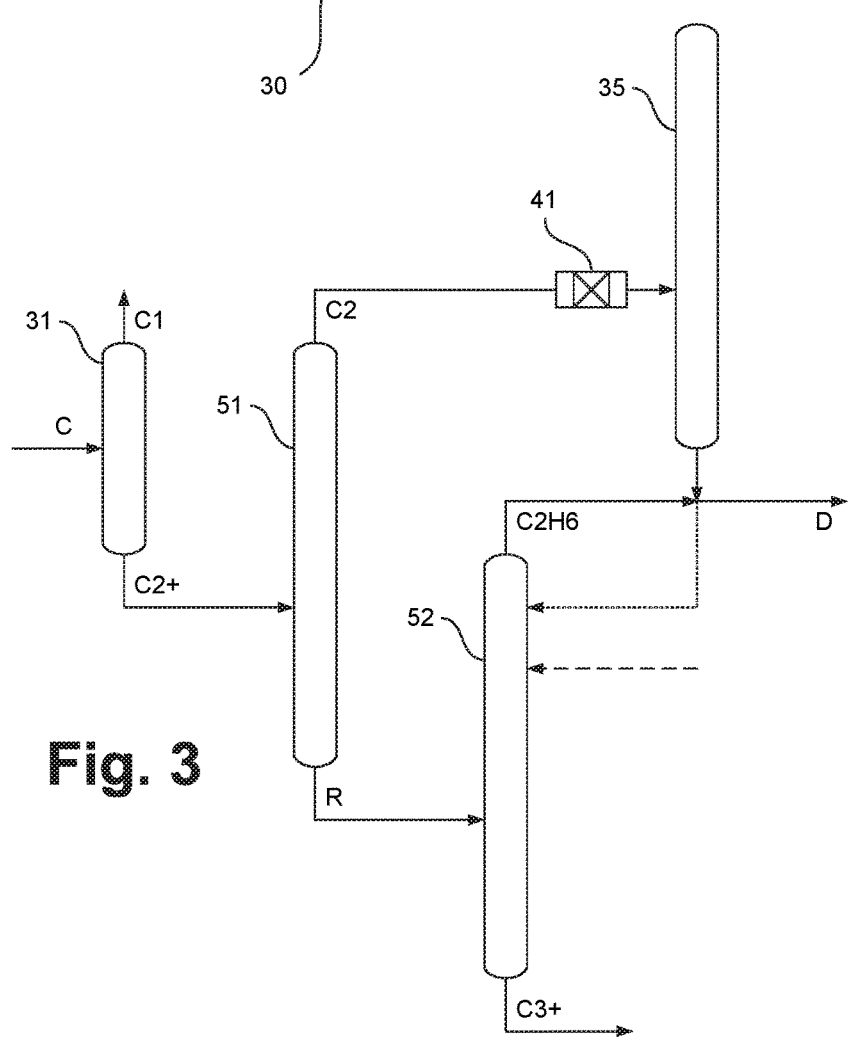
FIG. 3 schematically shows the sequence of a method for separating a hydrocarbon mixture in accordance with an embodiment of the invention.

FIG. 3 is another, alternative drawing of the method shown in FIG. 2. As can be seen from FIG. 3, the separation units 31, 35, 51 and 52 are implemented in corresponding systems in the form of distillation columns.

FIG. 4 again corresponds to FIG. 2 and shows an embodiment of the invention in which the hydrocarbon mixture or cracked gas C is separated by the "deethaniser-first" principle. As described, this means that, in a first separation unit 37 provided therein, a fraction which contains the predominant proportion of the hydrocarbons having two or fewer carbon atoms contained in the cracked gas C is formed from the cracked gas C. However, when (more) ethane-rich fresh charges are steam cracked, this C2minus fraction has ethane contents which are just as high as before, and which potentially could not be tolerated in conventional separation systems if they are set up for separating cracked gases which are obtained by steam cracking low-ethane fresh charges.

A separation unit 33 set up for processing the C3plus hydrocarbons is merely shown schematically here, but may also be present along with downstream devices.

Also, therefore, in an additional separation unit 53, a fraction S containing ethane is initially separated from the first fraction, in this case from the initially present C2minus fraction downstream from the separation unit 37, specifically in an amount which reduces the ethane content in the remaining C2minus fraction downstream from the separation unit 53 to a tolerable level, e.g. to less than 25%. Unlike previously, in this case this fraction containing ethane does not contain any significant amounts of heavier components, in other words C3plus hydrocarbons.

As shown previously in FIG. 1, the C2minus fraction is supplied to a separation unit 38, which operates as described in relation to FIG. 2B. However, because of the upstream separation unit 53, this has to process a much smaller amount of ethane.

Figure 4:
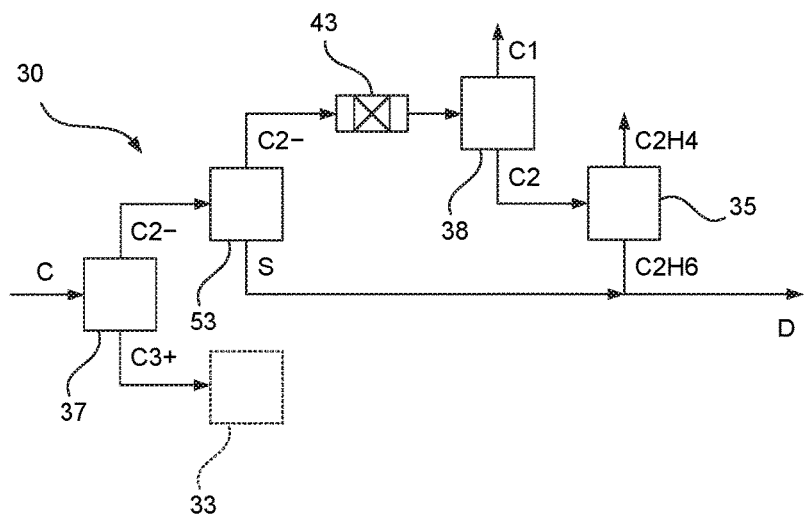
FIG. 4 schematically shows the sequence of a method for separating a hydrocarbon mixture in accordance with an embodiment of the invention.

The hydrogenation unit 43 is preferably arranged as shown in FIG. 4 (cf. different arrangement from FIG. 1), in such a way that it only has to process the C2minus stream downstream from the additional separation unit 53.

As an alternative to the arrangement shown in FIG. 4 of the additional separation unit 53, downstream from the separation unit 37, it may also for example be provided in parallel with the separation unit 37 or downstream from the separation unit 38 for processing the C2 stream which occurs there.

Figure 5:
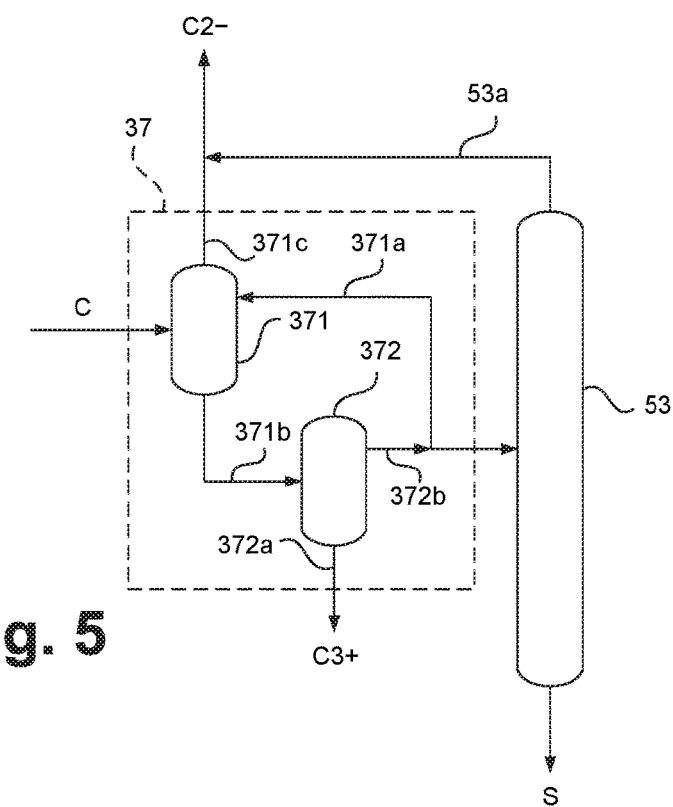
FIG. 5 schematically shows the sequence of a method for separating a hydrocarbon mixture in accordance with an embodiment of the invention.

FIG. 5 shows the first of these alternatives, specifically the arrangement in parallel with the separation unit 37. The separation unit 37 is shown in detail together with the additional separation unit 53.

In the example shown, the separation unit 37 comprises a first separation device 371 and a second separation device 372 (also known as a double column).

The cracked gas C is supplied to the first separation device 371. The first separation device 371 is operated using a liquid return stream 371a. A bottom product, which still contains substantially all of the components of the cracked gas C, precipitates in the bottom of the first separation device 371. This is drawn off as a stream 371b and fed into the second separation device 372. At the head of the first separation device 371, a head stream 371c is drawn off, which is a C2minus stream, of which the ethane content can be set inter alia by way of the amount of the return stream 371a.

In the second separation device 372, a bottom product 372a in the form of a C3plus fraction low in or free from other hydrocarbons is obtained. In an upper region of this second separation device 372, a stream 372b is drawn off and passed on in part (after condensation in a condenser, not shown) to the first separation device 371 as the liquid return stream 371a, and transferred in part into the separation unit 53, which is for example in the form of a distillation column as described previously.

As described previously, the separation unit 53 is formed so as to separate off the fraction S containing ethane. The fraction S containing ethane (and possibly further containing residues of C3plus hydrocarbons) is the bottom product of this separation unit 53. By contrast, a stream 53a, which also contains other hydrocarbons having three carbon atoms as well as ethane (which is not precipitated in the bottom of the separation unit 53), is drawn off from the head of this separation unit. This stream can thus be united with the head stream 371c drawn off at the head of the first separation device 371.

The united streams 53a and 371c correspond to a C2minus stream, such as is obtained in the separation unit 53 in accordance with FIG. 4.

The invention claimed is:

1. A method for separating a hydrocarbon mixture comprising:
    steam cracking a feed to produce a hydrocarbon mixture comprising at least hydrocarbons having one, two and three carbon atoms, including ethane and ethylene;

separating the hydrocarbon mixture in a demethanizer to produce a first fraction comprising at least 50% of the hydrocarbons having two or more carbon atoms;

separating the first fraction in a separation unit downstream of the demethanizer to produce a fraction R comprising ethane and a C2 fraction, wherein the fraction R comprising ethane comprises less than 10% of other hydrocarbons having two carbon atoms, wherein the C2 fraction comprises at least 50% ethane and ethylene but less than 25% ethane;

separating the C2 fraction in a C2 separation unit to produce an ethane fraction and an ethylene fraction; and separating at least part of the fraction R comprising ethane in a deethanizer.

2. The method according to claim 1, further comprising:
specifying a maximum acceptable ethane content which can be tolerated in a separation system for the method of separating the hydrocarbon mixture; and
adapting the amount of ethane in the fraction R comprising ethane in accordance therewith.

3. The method according to claim 1, wherein the C2 fraction comprises less than 20% ethane.

4. The method according to claim 1, wherein the fraction R comprising ethane comprises less than 1.5% ethylene.

5. The method according to claim 4, wherein at least a portion of the fraction R comprising ethane is passed to the steam cracking.

6. The method according to claim 1, further comprising: hydrogenating the hydrocarbon mixture or the first fraction.

7. A method for separating a hydrocarbon mixture comprising:

steam cracking a feed to produce a hydrocarbon mixture comprising at least hydrocarbons having one, two and three carbon atoms, including ethane and ethylene;

separating the hydrocarbon mixture in a deethanizer to produce a first fraction comprising at least 50% of the hydrocarbons having two or less carbon atoms;

separating a fraction S comprising ethane, wherein the fraction S comprising ethane is separated in parallel with or downstream of the deethanizer, wherein the fraction S comprising ethane comprises less than 10% of other hydrocarbons having two carbon atoms, wherein separation of the fraction S comprising ethane in parallel with the deethanizer comprises separating from at least a portion of the hydrocarbon mixture separated from the deethanizer the fraction S comprising ethane and a remaining fraction comprising less than 25% ethane, and combining the remaining fraction with the first fraction to produce a C2- fraction, and wherein separation of the fraction S comprising ethane downstream of the deethanizer comprises separating the fraction S comprising ethane from the first fraction and producing a C2- fraction comprising less than 25% ethane;

separating the C2- fraction in a demethanizer to produce a C2 fraction comprising at least 50% ethane and ethylene; and separating the C2 fraction in a C2 separation unit to produce an ethane fraction and an ethylene fraction.

8. The method according to claim 7, further comprising:
specifying a maximum acceptable ethane content which can be tolerated in a separation system for the method of separating the hydrocarbon mixture; and
adapting the amount of ethane in the fraction S comprising ethane in accordance therewith.

9. The method according to claim 7, wherein the first fraction after the fraction S comprising ethane is separated comprises less than 20% ethane.

10. The method according to claim 7, wherein the fraction S comprising ethane comprises less than 1.5% ethylene.

11. The method according to claim 10, wherein the fraction S comprising ethane is passed to the steam cracking.

12. The method according to claim 7, further comprising: hydrogenating the hydrocarbon mixture.

* * * * *